United States Patent [19]

Hartle et al.

[11] 4,280,819
[45] Jul. 28, 1981

[54] DIESEL FUEL COMPOSITIONS CONTAINING CERTAIN AZIDES FOR IMPROVED CETANE NUMBER

[75] Inventors: Robert J. Hartle, Gibsonia; Gary M. Singerman, Monroeville, both of Pa.

[73] Assignee: Gulf Research & Development Company, Pittsburgh, Pa.

[21] Appl. No.: 145,369

[22] Filed: Apr. 30, 1980

[51] Int. Cl.³ .................................................. C10L 1/22
[52] U.S. Cl. ............................................. 44/64; 44/65
[58] Field of Search .............. 44/64, 65; 260/239 AD, 260/349

[56] References Cited

U.S. PATENT DOCUMENTS

| 2,225,879 | 12/1940 | Miller et al. ............................. 44/64 |
| 3,242,166 | 3/1966 | Krespan et al. .................. 260/239 A |
| 3,534,016 | 10/1970 | Lange ..................................... 44/59 |

Primary Examiner—Winston A. Douglas
Assistant Examiner—Y. Harris-Smith
Attorney, Agent, or Firm—Deane E. Keith; Forrest D. Stine; Richard C. Gaffney

[57] ABSTRACT

Diesel fuel compositions which contain minor amounts of azides having the formula:

$$X=N^+=N^-$$

where X is selected from the group consisting of

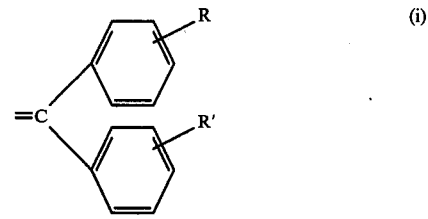 (i)

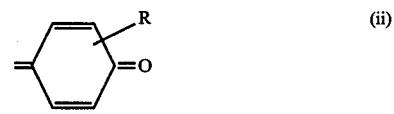

(ii)

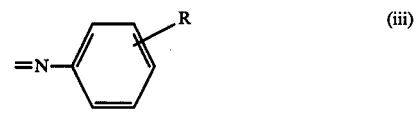

(iii)

where R and R' can be the same or different and are selected from the group consisting of hydrogen; alkyl straight- and branched chain hydrocarbons having from 1 to 8 carbon atoms; alkoxy groups having from 1 to 8 carbon atoms; aryl; aryloxy; nitro; hydroxy; halo; amino (except ortho to the azido); alkylamino; acyl groups having from 2 to 8 carbon atoms; alkylamido; and carbalkoxy. The minor amount of the azides in part improved cetane numbers (low ignition delay) to the diesel fuel.

9 Claims, No Drawings

DIESEL FUEL COMPOSITIONS CONTAINING CERTAIN AZIDES FOR IMPROVED CETANE NUMBER

SUMMARY OF THE INVENTION

This invention relates to diesel fuel compositions of improved cetane number and more particularly to diesel fuel compositions containing minor amounts of certain defined azides which impart the improved cetane number to the fuel.

DESCRIPTION OF THE INVENTION

In the manufacture of fuel for use in diesel-type internal combustion engines, and reaction-type engines, it has been found that many of the petroleum oil fractions or synthetic oil fractions whose boiling range viscosity and other physical characteristics render them potentially suitable for such use have improper combustion or ignition characteristics. In the case of diesel fuels, the unsatisfactory ignition qualities take the form of too great a time lag between injection of the fuel into the cylinder and the spontaneous ignition of the fuel near the end of the compression stroke, with consequent knocking, smoking and uneven running of the engine. The extent of the time lag or ignition delay of a diesel fuel is conveniently evaluated by a determination of its so-called cetane number. Cetane numbers can, for example, be determined by ASTM test D-613. In brief, the cetane number of a fuel may be defined as the percent by volume of cetane in a blend of cetane and alphamethylnaphthalene which has the same combustion characteristics as the fuel in question. A high cetane number indicates a low ignition delay period, and hence better performance as a diesel fuel. In the case of jet fuels, a similar problem is encountered in that a delay in ignition of the jet fuel upon injection of the fuel into the engine prevents optimum performance of the reaction engine. Thus an increase in the cetane number of a fuel corresponds to a decrease in the ignition delay period, which is desirable in both diesel fuel and jet fuel.

In view of the relatively low cetane numbers of many petroleum or synthetically derived oil fractions, i.e. from coal or shale oil, which are otherwise suited for use as diesel fuels, it has been proposed to blend with such fractions additive materials which have the property of decreasing the ignition delay period, of increasing the cetane number of the fraction. Improvement of the ignition characteristics of jet fuels by various additives has similarly been proposed. In analogous fashion, materials are added to gasoline motor fuel to improve the antiknock characteristics of the gasoline. Normally materials which improve antiknock characteristics do not improve cetane number, and vice-versa. This is to be expected, however, since antiknock additives are used to control combustion, whereas cetane improvers are used to speed combustion.

In accordance with the invention, improved fuel compositions have now been found for use in diesel engines and jet engines, which compositions comprise a major amount of a hydrocarbon fuel oil and a minor amount, sufficient to increase appreciably the burning rate of the fuel, of a compound having the formula:

where X is selected from the group consisting of:

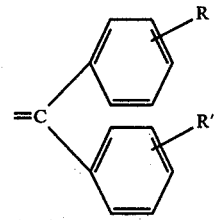

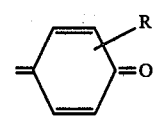

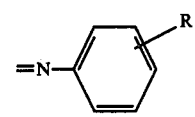

where R and R' can be the same or different and are selected from the group consisting of hydrogen; alkyl straight- and branched-chain hydrocarbons having from 1 to 8 carbon atoms; alkoxy groups having from 1 to 8 carbon atoms; aryl; aryloxy; nitro; hydroxy; halo (except fluorine); amino (except ortho to the azido); alkylamino; acyl groups having from 2 to 8 carbon atoms; alkylamido; and carbalkoxy.

Particularly preferred among the compounds set forth above are those in which R and R' may be hydrogen, methyl, methoxy, ethyl, ethoxy, propyl, n-butyl, tertiary butyl, tertiary octyl, cyclohexyl, chloro, or nitro.

To further illustrate the types of compounds falling within the scope of the above generic formula, the following specific examples of compounds are presented but are not meant in any way to limit the scope of the invention:

(i)

diphenyldiazomethane;
bis(4-methylphenyl)diazomethane;
bis(3-methylphenyl)diazomethane;
bis(2-methylphenyl)diazomethane;
bis(2,4-dimethylphenyl)diazomethane;
bis(2,4,6-trimethylphenyl)diazomethane;
bis(2-ethylphenyl)diazomethane
bis(2-tert.butylphenyl)diazomethane;
bis(4-tert.octylphenyl)diazomethane;
bis(4-methoxyphenyl)diazomethane;
bis(2-methoxyphenyl)diazomethane;
bis(3-methoxyphenyl)diazomethane;
bis(2,4-dimethoxyphenyl)diazomethane;
bis(2-methyl-4-methoxyphenyl)diazomethane;
4-methylphenyl-4'-methoxyphenyldiazomethane;
4-methoxyphenylphenyldiazomethane;
bis(2-n-butoxyphenyl)diazomethane;
bis(4-nitrophenyl)diazomethane;
bis(2,4-dinitrophenyl)diazomethane;
di-1-naphthyldiazomethane;
di-2-naphthyldiazomethane;
bis-1-(3-methylnaphthyl)diazomethane;
bis(3-chlorophenyl)diazomethane;
bis(2,4-dichlorophenyl)diazomethane
bis(4-phenoxyphenyl)diazomethane;
bis(4-hydroxyphenyl)diazomethane;
bis(3-aminophenyl)diazomethane;

bis[3-(N,N-dimethylamino)phenyl]diazomethane;
bis(4-acetophenyl)diazomethane;
bis(4-acetamidophenyl)diazomethane;
bis(3-ethoxycarbonylphenyl)diazomethane;

(ii)

1,4-benzoquinonediazide;
2,6-dimethyl-1,4-benzoquinonediazide;
2,6-dibutyl-1,4-benzoquinonediazide;
2,3,5,6-tetramethyl-1,4-benzoquinonediazide;
2,6-ditert.octyl-1,4-benzoquinonediazide;
2-n-hexyl-1,4-benzoquinonediazide;
2,6-dimethoxy-1,4-benzoquinonediazide;
2,6-tert.butyl-1,4-benzoquinonediazide;
2,6-dinitro-1,4-benzoquinonediazide;
2,3,5,6-tetrachloro-1,4-benzoquinonediazide;
2,6-diphenyl-1,4-benzoquinonediazide;
2,6-dibromo-1,4-benzoquinonediazide;
2(N,N-dimethylamino)1,4-benzoquinonediazide;
2-acetyl-1,4-benzoquinonediazide;
2-amino-1,4-benzoquinonediazide;
2-acetamido-1,4-benzoquinonediazide;

(iii)

phenylazide;
o-azidotoluene;
m-azidotoluene;
p-azidotoluene;
2,4-dimethylphenylazide;
2,3,4-trimethylphenylazide;
2,6-ditert.butylphenylazide;
2-n-octylphenylazide;
4-n-hexylphenylazide;
4-isopropylphenylazide;
4-methoxyphenylazide;
2,4-dimethoxyphenylazide;
4,n-butoxyphenylazide;
2-azidobiphenyl;
2,1-diazidobiphenyl;
1-azidonaphthalene;
2-azidonaphthalene;
4-phenoxyphenylazide;
4-cyclohexylphenylazide;
2-nitrophenylazide;
4-nitrophenylazide;
p-azidophenol;
2-chlorophenylazide;
3-chlorophenylazide;
4-fluorophenylazide;
2,4-dibromophenylazide;
m-azidoaniline;
p-azidoaniline;
3-azido-4,5-dimethylaniline;
2-methoxy-5-azidoaniline;
3-azido-1-naphthylamine;
2-azidobenzophenone;
4-azidophenyl-n-octyl ketone;
p-azidobenzyl alcohol;
p-azidoacetanilide;
4-N,N-dimethylaminophenylazide;
methyl p-azidobenzoate;
ethyl o-azidobenzoate The above compounds can be prepared by methods well known in the art for such compounds are not new compositions per se. Specific syntheses for those compounds within the scope of the generic formulas set forth above which were used in the working examples will be provided below. The diesel fuel or jet fuel compositions of this invention desirably contain from about 0.1 to about 50 grams of azide per gallon of fuel oil. The preferred range of concentration of the additive is from 4 to about 25 grams per gallon. The additive compounds utilized in the working examples below were blended into the base fuel at concentrations ranging from 4 to 16 grams per gallon.

The invention will be further described with reference to the following experimental work.

EXAMPLE 1

(Preparation of bis(4-methoxyphenyl)diazomethane)

25 grams (0.1 moles) of p,p'-dimethoxybenzophenone, which was purchased from the Aldrich Chemical Company, was dissolved in 50 ml of n-propanol and with solution was treated with 20 grams of hydrazine, which had been freshly distilled over sodium hydroxide pellets. The mixture was then refluxed for a total of 12 hours, after which the solvent (n-propanol) and excess hydrozine were removed at reduced pressure. The residual crude hydrazone was recrystallized from ethanol and had a melting point of 85° C.

The hydrazone (12.8 g–0.057 mole) was then added to 100 ml of low-boiling petroleum ether in a pressure bottle. Mercuric oxide (11.0 g) was then added and the bottle was sealed and then shaken for about 8 hours. External cooling was applied during the first hour of oxidation to maintain the temperature at about 20° C. The contents of the bottle were then filtered, and the filtrate evaporated. After evaporation the residual dark red crystals of bis(4-methoxyphenyl)diazomethane were recovered and were found to melt at 98°–100° C. with decomposition. References to this preparation and the preparation for similar compounds can be found in "Organic Synthesis", Coll. Vol. II, p. 496; "Organic Synthesis", Coll. Vol. III, p. 351; and Shirley, "Preparation of Organic Intermediates", p. 134.

EXAMPLE 2

A diesel fuel A having the composition shown on Table 1 was tested for its cetane number by ASTM Test D-613 and found to have a cetane number of 44.1.

15.6 grams of the azide prepared in Example 1 were then blended with diesel fuel A and the blend was found to have a cetane number of 47.6, for an increase in cetane number due to the presence of the azide of 3.5.

EXAMPLE 3

(Preparation of 2,6-Dimethyl-1,4-benzoquinonediazide)

2,6-dimethylbenzoquinone-1,4 purchased from the Aldrich Chemical Company was converted to the 4-tosylhydrazone following the procedure of Ried and Dietrich (Ber. 1961 387). The quinone (25 g–0.18 mole) was dissolved in 200 ml of methanol. This solution was then added dropwise to a solution of 35 g of p-tosylhydrazide in 150 ml of methanol containing 20 ml of concentrated hydrochloric acid. The addition was carried out at a temperature of about −10° C. The product was then separated from the mixture as orange crystals; was removed on a filter and recrystallized from methanol. The recrystallized product was found to have a melting point of 143°–148° C.

The tosylhydrazone (12.0 g) was added to 200 ml of methylene chloride, 100 ml of water, and 100 grams of ice in a separatory funnel. Sodium hydroxide solution (40 ml, 1 N) was added and the mixture was shaken for about 5 minutes. The methylene chloride layer was removed. The water layer was extracted with 50 ml of methylene chloride, which was then combined with the original methylene chloride layer. After washing with water, the methylene chloride was removed at reduced pressure below 40° C. The residue was 2,6-dimethyl-1,4-benzoquinonediazide.

EXAMPLE 4

A sufficient amount of the azide made in Example 3 above was blended with diesel fuel A to result in a concentration of 8.9 grams per gallon (0.06 mole per gallon). The resulting blend had a cetane number by ASTM Test D-613 of 52.3, showing an increase over the base fuel of 8.2.

EXAMPLE 5

Example 4 was repeated except the compound of Example 3 was blended with a No. 2 fuel oil whose properties are also shown on Table 1 below, and which have a cetane number of 41.9, to result in a blended product having a cetane number of 54.8 for an increase over the base fuel of 4.9.

The results of Examples 1 through 5 above are summarized on Table 2 below.

A series of arylazides was prepared using the procedure described in P.A.S. Smith et al, J. Am. Chem. Soc., 84 485 (1962). The specific preparation of 2-methoxy-b 5-azidoaniline will be specifically set forth below, with the understanding that those aryl azides which will be described in other examples below and on Table 2, which do not contain an amino substituent (compounds labeled 3, 6, 7 and 8 in Table 2) were prepared from the corresponding aniline following the procedure of step 3 below in Example 6.

EXAMPLE 6

(Preparation of 2-methoxy-5-azidoaniline)

The 2-methoxy-5-azidoaniline was prepared by the following steps:
(1) 2-methoxy-5-nitroaniline (16.8 g–0.1 mole) was fused with 16 g of phthalic anhydride. The mixture was held at 180°–210° C. with slow stirring until evolution of water was complete (about 2 hours). The solid cake was crushed and extracted three times with boiling ethanol. The residue was 2-methoxy-5-nitrophenylphthalimide, which was found to have a melting point of 280° C.
(2) 27.7 grams of the product from step 1 were dissolved in 900 ml of boiling acetone in a 2-liter flask. Acetic acid (90 ml) and water (90 ml) were then added. The mixture was stirred and refluxed while 90 grams of iron powder were added over gradually over a three-hour period. The mixture was then filtered while hot, and the filtrate was neutralized with a saturated sodium carbonate solution. The separated acetone layer was filtered into about 4 liters of ice water. 2-methoxy-5-aminophenylphthalimide was separated as a green crystalline solid, which was found to have a melting point of 232° C. after washing and drying.
(3) 24 grams of the wet product from step 2 was added to 600 ml of water containing 90 ml of hydrochloric acid. The suspension was cooled to 0°–5° C. and then diazotized with a solution of 6 grams of sodium nitrite in 25 ml of water. The mixture was stirred 4 hours at 0°–5° C. and then filtered. The filtrate was treated with a solution of 5 grams of sodium azide in 25 ml of water by dropwise addition. The mixture was stirred for one hour until evolution of nitrogen was complete. The precipitated solid was removed on a filter, washed with water and then dried. 2-methoxy-5-azidophenylphthalimide was found to melt at 171°–175° C. with decomposition and evolution of nitrogen.
(4) 10 grams of the product from step 3 were added to 100 ml of 95 percent methanol and treated with 1.2 grams of hydrazine (95%). After stirring for 90 minutes, the thick paste was dissolved by the addition of 51 ml of water and 15 ml of 20% sodium hydroxide solution. This solution was filtered into 1 liter of ice water. 2-methoxy-5-azidoaniline separated as a fluffy gray solid which was removed on a filter, washed with water, and vacuum dried. The melting point of this 2-methoxy-5-azidoaniline was found to be 51°–53° C.

EXAMPLES 7–12

A series of diesel fuel compositions were then tested for cetane ratings by ASTM Test D-613 on a diesel fuel B, whose properties are shown on Table 1 below, alone and blended with various aryl azides prepared as in Example 6 above.

In all of the Examples 7–12, a sufficient amount of the aryl azide was blended with the diesel fuel B to result in a concentration of 8 grams of the azide per gallon of the diesel fuel B. The specific aryl azides used in Examples 7–12, respectively, were phenyl azides; 2-methoxy-5-azidoaniline; m-azidoaniline; o-nitrophenylazide; o-azidotoluene; and, finally, o-chlorophenylazide. The results of all of these runs 7–12 are shown on Table 2 below.

TABLE 1

| PROPERTIES OF BASE FUELS | | | | |
|---|---|---|---|---|
| | Diesel Fuel | | No. 2 Fuel Oil | Kerosene |
| | A | B | | |
| Gravity, °API | 35.0 | 36.0 | 36.5 | 42.7 |
| Distillation | | | | |
| 1st drop, °F. | 363 | 357 | 330 | 340 |
| 10% evaporated, °F. | 420 | 422 | 421 | 382 |
| 50% evaporated, °F. | 483 | 495 | 497 | 425 |
| 90% evaporated, °F. | 573 | 594 | 586 | 476 |
| End Point, °F. | 635 | 651 | 643 | 522 |
| Recovery, % | 99.0 | 99.0 | 98.7 | 99.0 |
| Viscosity, SSU @ 100° F. | 34.4 | 34.6 | — | — |
| Pour Point, °F. | −55 | — | — | −60 |
| Aniline Point, °F. | 137 | 144 | — | −60 |
| Flash Point, PMCC, °F. | 136 | 154 | — | 110 |
| Sulfur, wt % | 0.06 | 0.09 | — | 0.10 |
| Cetane Number | 44.1 | 46.1–47.3 | 49.9 | 46.5 |

TABLE II

| CETANE NUMBER IMPROVEMENT | | | | | | | | | | | | | |
|---|---|---|---|---|---|---|---|---|---|---|---|---|---|
| Example No. Base Fuel, % by Vol. | Base Fuel | 2 | 4 | Base Fuel | 5 | Base Fuel | 7 | 8 | 9 | Base Fuel | 10 | 11 | 12 | Base Fuel | 13 |
| Diesel Fuel A | 100 | 100 | 100 | — | — | — | — | — | — | — | — | — | — | — | — |
| Diesel Fuel B | — | — | — | — | — | 100 | 100 | 100 | 100 | 100 | 100 | 100 | 100 | — | — |

TABLE II-continued

CETANE NUMBER IMPROVEMENT

| Example No. Base Fuel, % by Vol. | Base Fuel | 2 | 4 | Base Fuel | 5 | Base Fuel | 7 | 8 | 9 | Base Fuel | 10 | 11 | 12 | Base Fuel | 13 |
|---|---|---|---|---|---|---|---|---|---|---|---|---|---|---|---|
| No. 2 Heating Oil | — | — | — | 100 | 100 | — | — | — | — | — | — | — | — | — | — |
| Kerosene | — | — | — | — | — | — | — | — | — | — | — | — | — | 100 | 100 |
| Additive, grams/gallon (moles/gallon) | | | | | | | | | | | | | | | |
| (1) bis(4-methoxylphenyl) diazomethane | — | 15.6 (0.06) | — | — | — | — | — | — | — | — | — | — | — | — | — |
| (2) 2,6-dimethyl-1,4-benzoquinonediazide | — | — | 8.9 (0.06) | — | 8.9 (0.06) | — | — | — | — | — | — | — | — | — | — |
| (3) phenyl azide | — | — | — | — | — | — | 8.0 (0.07) | — | — | — | — | — | — | — | — |
| (4) 2-methoxy-5-azidoaniline | — | — | — | — | — | — | — | 8.0 (0.05) | — | — | — | — | — | — | — |
| (5) m-azidoaniline | — | — | — | — | — | — | — | — | 8.0 (0.06) | — | — | — | — | — | — |
| (6) o-azidotoluene | — | — | — | — | — | — | — | — | — | — | 8.0 (0.05) | — | — | — | — |
| (7) o-azidotoluene | — | — | — | — | — | — | — | — | — | — | — | 8.0 (0.06) | — | — | — |
| (8) o-chlorophenylazide | — | — | — | — | — | — | — | — | — | — | — | — | 8.0 (0.05) | — | — |
| (9) o-azidoaniline | — | — | — | — | — | — | — | — | — | — | — | — | — | — | 4.0 (0.03) |
| Cetane Number ASTM D 613 | 44.1 | 47.6 | 52.3 | 49.9 | 54.8 | 46.1 | 49.4 | 52.1 | 48.2 | 47.3 | 48.7 | 50.4 | 51.3 | 46.5 | 45.1 |
| Change in cetane number | — | +3.5 | +8.2 | — | +4.9 | — | +3.3 | +6.0 | +2.1 | — | +1.4 | +3.1 | +4.0 | — | −1.4 |

Referring to Table 2, it can be seen that the diesel fuel B had a cetane number of 46.1 (one batch) and 47.3 (a second batch). The addition of the phenyl azides resulted in an increase in diesel number in all instances.

A review of Table 2 shows that the most effective compound tested for increasing cetane number was 2,6-dimethyl-1,4-benzoquinonediazide (Example 4), which gave an 8.2 cetane number increase at a concentration of 8.9 grams (0.06 mole per gallon).

EXAMPLE 13

Four grams per gallon (0.03 mole per gallon) of o-azidoaniline were added to kerosene, and a decrease in cetane number of 1.4 was observed. The properties of the kerosene are shown on Table 1, and the cetane number of the blended product is shown on Table 2.

It is to be understood that the above disclosure is by way of specific examples and that numerous variations and modifications are available to those with ordinary skill in the art without departing from the true spirit of the scope of this invention.

We claim:

1. An improved fuel composition comprising a major amount of a hydrocarbon fuel oil selected from the group consisting of diesel fuel and jet fuel and a minor amount sufficient to increase the cetane number of the fuel of an additive compound having the following structural formula:

$$X=N^+=N^-$$

where X is selected from the group consisting of:

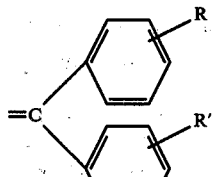
(i)

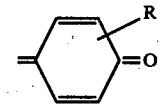
(ii)

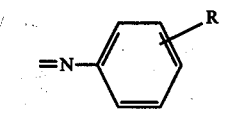
(iii)

where R and R' can be the same or different and are selected from the group consisting of hydrogen; alkyl straight- and branched chain hydrocarbons having from 1 to 8 carbon atoms; alkoxy groups having from 1 to 8 carbon atoms; aryl; aryloxy; nitro; hydroxy; halo amino in a position meta or para to the azido; alkylamino; acyl groups having from 2 to 8 carbon atoms; alkylamido; and alkoxy carbonyl.

2. A composition according to claim 1 wherein said minor amount is about 0.1 to about 50 grams per gallon of the final fuel composition.

3. A composition according to claim 2 wherein X has the structural formula:

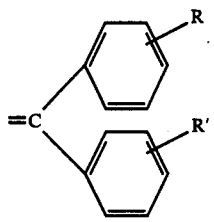

4. A composition according to claim 2 wherein X has the structural formula:

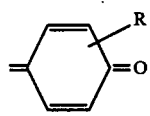

5. A composition according to claim 2 wherein X has the structural formula:

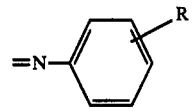

6. An improved fuel composition comprising a major amount of a hydrocarbon fuel oil selected from the group consisting of diesel fuel and jet fuel and a minor amount sufficient to increase the cetane number of such fuel oil of bis(4-methoxy-phenyldiazomethane).

7. An improved fuel composition comprising a major amount of a hydrocarbon fuel oil selected from the group consisting of diesel fuel and jet fuel and a minor amount sufficient to increase the cetane number of such fuel oil of 2,6-dimethyl-1,4-benzoquinonediazide.

8. An improved fuel composition comprising a major amount of a hydrocarbon fuel oil selected from the group consisting of diesel fuel and jet fuel and a minor amount sufficient to increase the cetane number of such fuel oil of phenyl azide.

9. An improved fuel composition comprising a major amount of a hydrocarbon fuel oil selected from the group consisting of diesel fuel and jet fuel and a minor amount sufficient to increase the cetane number of such fuel oil of 2-methoxy-5-azidoaniline.

* * * * *